US008389530B2

(12) United States Patent
Leriche et al.

(10) Patent No.: US 8,389,530 B2
(45) Date of Patent: Mar. 5, 2013

(54) SUBSTITUTED QUINAZOLINE COMPOUNDS

(75) Inventors: Caroline Leriche, Paris (FR); Eric Auclair, Montlhery (FR); Jacques Le Roux, Le Pre Saint Gervais (FR); David N. Middlemiss, Hertfordshire (GB)

(73) Assignee: Fovea Pharmaceuticals, Paris (FR)

( * ) Notice: Subject to any disclaimer, the term of this patent is extended or adjusted under 35 U.S.C. 154(b) by 0 days.

(21) Appl. No.: 13/142,333

(22) PCT Filed: Dec. 18, 2009

(86) PCT No.: PCT/EP2009/067494
§ 371 (c)(1),
(2), (4) Date: Sep. 21, 2011

(87) PCT Pub. No.: WO2010/076238
PCT Pub. Date: Jul. 8, 2010

(65) Prior Publication Data
US 2012/0004210 A1    Jan. 5, 2012

(30) Foreign Application Priority Data
Dec. 29, 2008  (EP) ..................................... 08360043

(51) Int. Cl.
*A01N 43/54* (2006.01)
*A61K 31/517* (2006.01)
*C07D 401/00* (2006.01)
(52) U.S. Cl. ...................... 514/266.1; 544/283; 544/284
(58) Field of Classification Search ............... 514/266.1; 544/283, 284
See application file for complete search history.

(56) References Cited

FOREIGN PATENT DOCUMENTS

| EP | 1878727 | * | 1/2008 |
| EP | 1878727 A1 | | 1/2008 |
| WO | WO 01/38315 | * | 5/2001 |
| WO | WO 01/38315 A1 | | 5/2001 |
| WO | WO2006-039718 | * | 4/2006 |
| WO | WO 2006/039718 A2 | | 4/2006 |
| WO | WO2008-079988 | * | 7/2008 |
| WO | WO 2008/079988 A2 | | 7/2008 |

OTHER PUBLICATIONS

Vippagunta et al.*
Henriksen et al., Tetrahedron Letters, vol. 47 (7), 2006.*
The International Search Report for International Patent Application No. PCT/EP2009/067494, dated Mar. 18, 2010.
Henriksen, et al., "2-Chloroquinazoline. Synthesis and reactivity of a versatile heterocyclic building block", *Tetrahedron Letters*, vol. 47, No. 47, 2006, pp. 8251-8254.
The Opposition filed in the Chilean Patent Office, against the corresponding Chilean Patent Application No. 1603-2011, dated Dec. 23, 2011, with the English Translation.
The Documents filed in the Chilean Patent Office on Jul. 25, 2012 in response to the Opposition Filing, in the Chilean Patent Application No. 1603-2011, with the English Translation.

* cited by examiner

*Primary Examiner* — Paul V. Ward
(74) *Attorney, Agent, or Firm* — Foley & Lardner LLP

(57) ABSTRACT

The invention is directed to certain novel compounds, methods for producing them and methods for treating or ameliorating a kinase-mediated disorder. More particularly, this invention is directed to substituted quinazoline compounds useful as selective kinase inhibitors, methods for producing such compounds and methods for treating or ameliorating a kinase-mediated disorder, In particular, the methods relate to treating or ameliorating a kinase-mediated disorder including cardiovascular diseases, diabetes, diabetes-associated disorders, inflammatory diseases, immunological disorders, cancer and diseases of the eye such as retinopathies or macular degeneration or other vitreoretinal diseases, and the like.

28 Claims, No Drawings

SUBSTITUTED QUINAZOLINE COMPOUNDS

CROSS-REFERENCE TO RELATED PATENT APPLICATIONS

This application is the U.S. National Phase of PCT/EP2009/067494, filed Dec. 18, 2009, which claims priority from European Patent Application No.: 08360043.7, filed Dec. 29, 2008, which are incorporated herein by reference in entirety.

The invention is directed to certain novel compounds, methods for producing them and methods for treating or ameliorating a disorder involving tyrosine kinase dysregulation such as disorder associated with increased vascular permeability or angiogenesis. More particularly, this invention is directed to substituted quinazoline compounds useful as selective kinase inhibitors, methods for producing such compounds and methods for treating or ameliorating a kinase-mediated disorder. In particular, the methods relate to treating or ameliorating a disorder involving tyrosine kinase dysregulation including cardiovascular diseases, diabetes, diabetes-associated disorders, inflammatory diseases, immunological disorders, cancer and diseases of the eye such as retinopathies or macular degeneration or other vitreoretinal diseases, and the like.

Passage of fluid and cells out of blood vessels is a significant contributing factor to inflammation, tissue injury, oedema and death in a variety of circumstances. These include ischemic injury, toxic shock, burns, trauma, allergic and immune reactions. Vascular permeability is regulated in part by cell-cell adhesions between endothelial cells. The endothelial cell monolayer lining the vasculature forms a barrier that maintains the integrity of the blood fluid compartment, but permits passage of soluble factors and leukocytes in a regulated manner. Dysregulation of this process results in vascular leakage into surrounding tissues, which accompanies the inflammation associated with pathological oedematous conditions. Vascular permeability is a finely tuned-up function that can positively contribute to protective immune responses and wound healing; however, in a number of pathological situations, massive and/or chronic leakage of fluid as well as migration of immune cells into tissues can have serious, and sometimes, life-threatening consequences.

Abnormal retinal vascular permeability leading to oedema in the area of the macula is the leading cause of vision loss in diseases such as diabetic retinopathy, exudative macular degeneration, retinal vascular occlusions, and inflammatory and neoplastic conditions. Although a variety of disease processes may lead to increased vascular permeability through different mechanisms, the cytokine VEGF is known to play a major role as inducer of vascular leakage. VEGF was first described as a potent vascular permeability factor (VPF) secreted by tumour cells that stimulated a rapid and reversible increase in microvascular permeability (Senger et al., 1983, Science., 25, 219, 983-5). Increased vascular permeability in ischemic retinopathies and possibly also in exudative macular degeneration and uveitis, for example, correlated with VEGF levels (Fine et al., 2001, Am. J. Ophthalmol., 132, 794-796; Boyd et al., 2002, Arch Ophthalmol., 120, 1644-1650) and VEGF antagonists have been successfully used to reduce retinal/macular oedema in neovascular eye diseases such as age-related macular degeneration leading to stabilization or even improvement of visual acuity in a subset of affected patients. The way by which VEGF induces vascular permeability has recently been unravelled (Gavard and Gutkind, 2006, Nat Cell Biol., 8, 1223-1234) and it has been shown that VEGF-induced vascular leakage is mediated by cytoplasmic protein kinase members of the Src proto oncogene family.

Protein kinases play a central role in the regulation and maintenance of a wide variety of cellular processes and cellular functions. For example, kinase activity acts as a molecular switch regulating cell proliferation, activation, and/or differentiation. It is now widely accepted that many diseases result from abnormal cellular responses triggered by overactive protein kinase-mediated pathways.

Src kinases form a family of membrane-attached non receptor-dependent tyrosine kinases encompassing eight members in mammals: Src, Fyn, Yes, Fgr, Lyn, Hck, Lck, and Blk (Bolen et al., 1997, Annu. Rev. Immunol, 15, 371) which have important roles in receptor signalling and cellular communication (Thomas and Brugge, 1997, Annu Rev Cell Dev Biol., 13, 513-609). While most Src kinases are broadly expressed (i.e. Src, Fyn, Yes), certain members of the family such as Hck, Blk or Lck exhibit a restricted expression. Src kinases play a pivotal role as membrane-attached molecular switches that link a variety of extracellular cues to intracellular signalling pathways. This is the basis for the involvement of Src kinases in cell proliferation and differentiation as well as cell adhesion and migration (Thomas S M and J S Brugge, 1997, supra).

It has been well-documented that Src protein levels and Src kinase activity are significantly elevated in human cancers including breast cancers, colon cancers, pancreatic cancers, certain B-cell leukemias and lymphomas, gastrointestinal cancer, non-small cell lung cancers, bladder cancer, prostate and ovarian cancers, melanoma and sarcoma (Summy and Gallick, 2003, Cancer Metastasis Rev, 22, 337-58). Thus, it has been anticipated that blocking signalling through the inhibition of the kinase activity of Src will be an effective means of modulating aberrant pathways that drive oncologic transformation of cells (Abram et al., 2000, Exp. Cell Res., 254, 1; Russi et al, 2006, JPET, 318, 161-172; Jallal et al., 2007, Cancer Research, 67, 1580-1588).

Similarly, it is well documented that Src-family kinases are also important for signalling downstream of immune cell receptors. Fyn, like Lck, is involved in TCR signalling in T cells (Appleby et al., 1992, Cell, 70, 751). Hck and Fgr are involved in Fcγ receptor signalling leading to neutrophil activation (Vicentini et al., 2002, J. Immunol., 168, 6446). Lyn and Src also participate in Fcγ receptor signaling leading to release of histamine and other allergic mediators (Turner and Kinet, 1999, Nature, 402, B24). These findings suggest that Src family kinase inhibitors may be useful in treating allergic diseases and asthma.

In accordance with the effect of VEGF on vascular permeability, several reports support a role of Src kinase in the development of oedema. For instance, Src but not Fyn deficiency or blockade of Src reduced brain oedema by about 55% following permanent cerebral ischemia in mice (Paul et al., 2001, Nat. Med., 7(2):222-7). Recently, PP1, a Src tyrosine kinase inhibitor was found to decrease oedema, to decrease breakdown of the brain-blood barrier (BBB), to reduce expression of VEGF (Jadhav et al., 2007, J. Neurosurg., 106, 680-686). Similarly, Scheppke et al. (2008, J Clin Invest., 118, 2337-2346) have shown that Src kinases are critical mediators of VEGF- and ischemia-induced retinal vascular leakage.

Furthermore, Src tyrosine kinases fully mediate VEGF receptor signalling in vascular endothelial cells. Thus, activation of Src kinases resulting from stimulation of VEGF receptor or other growth factor located on endothelial cells or progenitors triggers angiogenesis, a response which can be deleterious in retinal and corneal diseases and which markedly contributes to tumor development and metastasis migration.

Several classes of compounds have been disclosed that modulate or, more specifically, inhibit kinase activity as potential treatments of kinase-mediated disorders, particularly cancer.

For example, WO2001038315 describes aminoquinazolines as inhibitors of cyclin-dependent kinases.

WO2008068507 describes pyridinylquinazolines as Raf serine/threonine kinase inhibitors for treating cancer.

WO2008079988 describes quinazolines as PDK1 kinase inhibitors for treating proliferative diseases such as cancer.

WO2006118256 describes quinazoline derivatives as p38MAPK inhibitors for inhalation and for treating various inflammatory diseases and cancer.

WO2006039718 describes aryl nitrogen-containing bicyclic compounds for use in treating protein kinase-mediated disease, including inflammation, cancer and related conditions.

WO2005037285 describes 2,6-disubstituted bicyclic heterocycles as Raf serine/threonine kinase inhibitors for treating disorders such as cancer.

WO2004065378 describes 2-aminopyridines as cdk4 inhibitors for treating cell proliferative disorders such as cancer, atherosclerosis and restenosis.

Interestingly, WO2006024034 describes heterocyclic compounds derived from benzotriazine, triazines, triazoles and oxadiazoles, such as benzotriazine compounds (WO2005096784) or pyrimidine compounds (WO2006101977) which are capable of inhibiting kinases, such as members of the Src kinase family. Nevertheless, these drugs while they are claimed as potentially useful as for treatment of various ophthalmological diseases (e.g. age-related macular degeneration, diabetic retinopathy, diabetic macular oedema, cancer, and glaucoma) are lipophilic and water insoluble (see WO2006133411). According to the inventors of WO2006133411, these specific properties are particularly advantageous, particularly for ophthalmic uses, since these drugs being insoluble in water (water solubility of less than about 0.1 mg/mL at a pH range of 4-8) possess high efficiency of loading and negligible leakage due to high partitioning of the drug into the liposome used for delivering them compared to the water.

All the patents and publications mentioned above and throughout are incorporated in their entirety by reference herein.

The eye is a tightly protected organ. In this respect, treating diseases of the back-of-the-eye is probably the most difficult and challenging task of drug discovery as evidenced by the paucity of therapeutic options. One of the most convenient and safest forms of drug delivery to the eye is eye drops, since it is non invasive, does not require medical assistance and requests small volumes of drug solution. However, in order to be suitable for topical instillation, molecules have to be potent enough towards their molecular target, to present physicochemical properties allowing crossing of cell membranes, and to be sufficiently soluble in aqueous medium to be applied as solution onto the cornea. In addition, it is crucial that such drug molecules are as colourless as possible to prevent staining of ocular tissue which ultimately may interfere with vision. Furthermore, patients enrolled in clinical trials must not be aware of the nature of their treatment, which is obviously biased when the active ingredient preparation is "highly" coloured. Additionally, due to the multiple cross reactivity between kinases, it is highly desirable that said drug molecules inhibit the targeted kinases with a high degree of selectivity.

A feature of the present invention is to provide novel compounds which have increased water solubility compared to competitors.

Another feature of the present invention is to provide compounds that are highly potent, particularly towards src and lyn kinase inhibitors.

Another feature of the present invention is to provide compounds which are useful for treating a disorder, including an ophthalmic disorder, involving tyrosine kinase dysregulation such as disorder associated with increased vascular permeability or angiogenesis.

Another feature of the present invention is to provide compounds which are colourless or almost colourless, especially in solution.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

According to one embodiment, the invention concerns compounds having the structure (I) as well as a pharmaceutically acceptable salt, hydrate or solvate thereof:

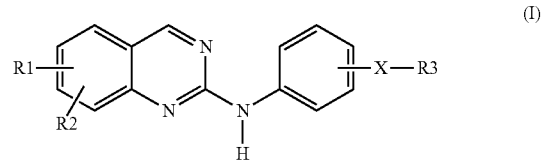

wherein:
R1 and R2 are hydrogen, C1-C4 alkyl, aryl, heteroaryl, —CN, -halogen, —CF$_3$, —OR4,
R3 is hydrogen, C1-C4 alkyl, cycloalkyl, heterocycloalkyl, aryl, heteroaryl, —CN, —CF$_3$, —OR4, —OCOR4-COR4, —NR4R5, —NR4COR5, —NR4COOR5, —(C1-C4 alkyl) OR4, —(C1-C4 alkyl)COR4, —(C1-C4 alkyl)NR4R5, —(C1-C4 alkyl)NR4COR5, —(C1-C4 alkyl)NR4COOR5,
X is a bond, or (CH$_2$)aW(CH$_2$)b, (CH$_2$)aW(CH$_2$)bY(CH$_2$)c or —[(CH$_2$)aW(CH$_2$)b]m-(Z)e-[(CH$_2$)cY(CH$_2$)d]n wherein:
  a, b, c and d are independently 0, 1, 2 or 3,
  e is 0, 1 or 2, and
  n and m are independently 0 or 1, and
  W is —CO—, —O—, —SO$_2$—, —CH$_2$—, —CHOH—, —NR6-, NR7CONR8 or NR7SO$_2$NR8, and
  Y is —CO—, —O—, —SO$_2$—, —CH$_2$—, —CHOH— or —NR6-, NR7CONR8 or NR7SO$_2$NR8 and
  Z is selected from the group consisting of cycloalkyl, heterocycloalkyl, aryl and heteroaryl, and when e is 2, then each Z moiety is selected independently from one another R4, R5 and R6 are independently hydrogen, C1-C4 alkyl and where R4 and R5 together can form a 5-7 membered ring, R7 and R8 are independently hydrogen, C1-C4 alkyl and where R7 and R8 together can form a 5-7 membered ring.

As used herein throughout the entire application, the terms "a" and "an" are used in the sense that they mean "at least one", "at least a first", "one or more" or "a plurality" of the referenced compounds or steps, unless the context dictates otherwise. More specifically, "at least one" and "one or more" means a number which is one or greater than one, with a special preference for one, two or three.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

As used herein, the term "comprising", "containing" when used to define products, compositions and methods, is intended to mean that the products, compositions and methods include the referenced compounds or steps, but not excluding others.

As used herein, the term "halogen" as a group or part of a group is generic for fluoro, chloro, bromo or iodo.

The term "cycloalkyl" means a saturated monocyclic carbocycle containing from 3 to 7 carbon atoms, more preferably from to 5 carbon atoms. Examples of monocyclic cycloalkyl radicals include cyclopropyl, cyclobutyl, cyclopentyl and the like.

The term "heterocycloalkyl" means a saturated mono- or bicyclic heterocycle having from 3 to 14 ring members, preferably from 5 to 10 ring members and more preferably from 5 to 6 ring members, which contains one or more heteroatom ring members selected from nitrogen, oxygen and sulphur and which is optionally substituted with R9 and/or R10 moities. Examples of heterocycloalkyl are pyrrolidine, piperidine, piperazine, morpholine and the like.

The term "aryl" includes mono- and bicyclic aromatic carbocycles, optionally substituted with R9 and/or R10 moities. Examples of aryl include phenyl, 1-naphthyl, 2-naphthyl.

The term "heteroaryl" means an aromatic mono- or bicyclic heterocycle having from 5 to 10 ring members, preferably from 5 to 6 ring members, which contains one or more heteroatom ring members selected from nitrogen, oxygen and sulphur and which is optionally substituted with R9 and/or R10 moities. Examples of heteroaryl are pyridine, indole, benzofuran, oxazole, triazole, pyrimidine and the like.

R9/R10 are independently selected from hydrogen, C1-C4 alkyl, cycloalkyl, heterocycloalkyl, aryl, heteroaryl, —CN, -halogen, —CF3, =O, —OR4, —NR4R5, —NR4COR5, —NR4COOR5, —(C1-C4 alkyl)OR4, —(C1-C4 alkyl)NR4R5, —(C1-C4 alkyl)NR4COR5, —(C1-C4 alkyl)NR4COOR5, —COOH, COOR4 with R4 and R5 as defined above.

The compounds of the invention may contain one or more chiral centres, because of the presence of asymmetric carbon atoms, and they may therefore exist as a number of diastereoisomers with R or S stereochemistry at each chiral centre. The invention includes all such diastereoisomers and mixtures thereof.

Prodrug forms of the compounds of Formula I are also part of the present invention. A prodrug may be a derivative of a biologically active substance (the "parent drug" or "parent molecule") that requires transformation within the body in order to release the active drug, and that has improved delivery properties over the parent drug molecule. The transformation in vivo may be, for example, as the result of a process, such as chemical or enzymatic hydrolysis of a carboxylic, phosphoric or sulphate ester, or reduction or oxidation of a susceptible functionality.

The term "compound" herein is in general referring to compounds of formula I, or a pharmaceutically acceptable salt, hydrate, solvate, crystal form, individual diastereomers or prodrugs thereof.

For use in accordance with the invention, the following structural characteristics are currently preferred, in any compatible combination, in the compounds (I):

R1 is preferably an aryl, more preferably a phenyl.

R1 is preferably substituted with R9 and R10 wherein R9/R10 is C1-C4 alkyl (preferably $CH_3$), halogen (preferably —Cl), or —OH.

R1 is preferably a phenyl and is substituted with R9 and R10 in positions 2, 5 or 6.

R2 is preferably hydrogen or methyl.

X is preferably a bond.

Alternatively X is preferably $(CH_2)aW(CH_2)b$ where a is 0, b is 2, W is —O—.

Alternatively X is preferably $(CH_2)aW(CH_2)bY(CH_2)c$ where a is 0, b is 1 and c is 0, W is —O— and Y is —CO—.

Alternatively X is preferably —[$(CH_2)aW(CH_2)b$]m-Z—[$(CH_2)cY(CH_2)d$]n where m is 0, n is 1, c is 0, d is 0 or 2, Y is —CO— or is absent and Z is imidazoline-2-one or a piperazine.

According to one embodiment, X is branched in position 3 or 4 of the phenyl moiety.

R3 is preferably C1-C4 alkyl, more preferably $CH_3$.

Alternatively R3 is a C1-C4 alkyl group, preferably a methyl group, substituted with R9 where R9 is preferably OH.

Alternatively R3 is preferably an heteroaryl group, preferably pyridine.

Alternatively R3 is preferably a heterocycloalkyl, preferably pyrrolidine, piperidine, azepine, piperazine or morpholine, more preferably pyrrolidine.

Alternatively R3 is preferably a heterocycloalkyl substituted with R9 where R9 is preferably —COOH, COOR4, —N[$CH_3$]$_2$.

Compounds of the invention include those of the Examples herein, in particular the following, and their salt, hydrate, solvate:

[6-(2,6-Dimethyl-phenyl)-quinazolin-2-yl]-[4-(2-pyrrolidin-1-yl-ethoxy)-phenyl]-amine;

4-Chloro-3-{2-[4-(2-pyrrolidin-1-yl-ethoxy)-phenylamino]-quinazolin-6-yl}-phenol;

(R)-1-(2-{4-[6-(2,6-Dimethyl-phenyl)-quinazolin-2-ylamino]-phenoxy}-ethyl)-pyrrolidine-2-carboxylic acid;

1-{4-[6-(2,6-Dimethyl-phenyl)-quinazolin-2-ylamino]-phenyl}-3-(2-pyrrolidin-1-yl-ethyl)-imidazolidin-2-one;

1-(4-{4-[6-(2,6-Dimethyl-phenyl)-quinazolin-2-ylamino]-phenyl}-piperazin-1-yl)-ethanone;

(4-{4-[6-(2,6-Dimethyl-phenyl)-quinazolin-2-ylamino]-phenyl}-piperazin-1-yl)-pyridin-4-yl-methanone;

1-{4-[6-(2-Chloro-5-hydroxy-phenyl)-quinazolin-2-ylamino]-phenyl}-3-(2-pyrrolidin-1-yl-ethyl)-imidazolidin-2-one;

2-{4-[6-(2-Chloro-5-hydroxy-phenyl)-quinazolin-2-ylamino]-phenoxy}-1-((R-3-dimethylamino-pyrrolidin-1-yl)-ethanone;

1-((R)-3-Dimethylamino-pyrrolidin-1-yl)-2-{4-[6-(2,6-dimethyl-phenyl)-quinazolin-2-ylamino]-phenoxy}-ethanone;

1-{4-[6-(2-Chloro-5-hydroxy-phenyl)-quinazolin-2-ylamino]-phenyl}-3-(2-methoxy-ethyl)-imidazolidin-2-one;

3-{2-[4-(2-Azepan-1-yl-ethoxy)-phenylamino]-quinazolin-6-yl}-4-chloro-phenol;

[6-(2,6-Dimethyl-phenyl)-quinazolin-2-yl]-(4-piperazin-1-yl-phenyl)-amine;

4-Chloro-3-{8-methyl-2-[4-(2-pyrrolidin-1-yl-ethoxy)-phenylamino]-quinazolin-6-yl}-phenol;

[(R)-1-(2-{4-[6-(2-Chloro-5-hydroxy-phenyl)-quinazolin-2-ylamino]-phenoxy}-acetyl)-pyrrolidin-3-yl]-dimethyl-ammonium;

[(R)-1-(2-{4-[6-(2-Chloro-5-hydroxy-phenyl)-quinazolin-2-ylamino]-phenoxy}-acetyl)-pyrrolidin-3-yl]-dimethyl-ammonium;

4-Chloro-3-[2-(3-hydroxymethyl-phenylamino)-8-methyl-quinazolin-6-yl]-phenol;

(R)-1-(2-{4-[6-(2-Chloro-5-hydroxy-phenyl)-8-methyl-quinazolin-2-ylamino]-phenoxy}-ethyl)-pyrrolidine-2-carboxylic acid;

1-{4-[6-(2-Chloro-5-hydroxy-phenyl)-8-methyl-quinazolin-2-ylamino]-phenyl}-3-(2-pyrrolidin-1-yl-ethyl)-imidazolidin-2-one;

(R)-1-[2-(3-{4-[6-(2-Chloro-5-hydroxy-phenyl)-8-methyl-quinazolin-2-ylamino]-phenyl}-2-oxo-imidazolidin-1-yl)-ethyl]-pyrrolidine-2-carboxylic acid;

1-{4-[6-(2-Chloro-5-hydroxy-phenyl)-8-methyl-quinazolin-2-ylamino]-phenyl}-3-[2-((R)-3-dimethylamino-pyrrolidin-1-yl)-ethyl]-imidazolidin-2-one;

1-(4-{4-[6-(2-Chloro-5-hydroxy-phenyl)-8-methyl-quinazolin-2-ylamino]-phenyl}-piperazin-1-yl)-ethanone;

(4-{4-[6-(2-Chloro-5-hydroxy-phenyl)-8-methyl-quinazolin-2-ylamino]-phenyl}-piperazin-1-yl)-pyridin-4-yl-methanone;

(4-{4-[6-(2-Chloro-5-hydroxy-phenyl)-8-methyl-quinazolin-2-ylamino]-phenyl}-piperazin-1-yl)-pyridin-3-yl-methanone;

(4-{4-[6-(2-Chloro-5-hydroxy-phenyl)-8-methyl-quinazolin-2-ylamino]-phenyl}-piperazin-1-yl)-pyridin-2-yl-methanone;

2-{4-[6-(2-Chloro-5-hydroxy-phenyl)-8-methyl-quinazolin-2-ylamino]-phenoxy}-1-((R)-3-dimethylamino-pyrrolidin-1-yl)-ethanone.

According to one embodiment, the compound of the Invention is a salt of compound of formula I. In specific embodiment, said salt is chlorhydrate.

According to one preferred embodiment, the compounds of the Invention have a water solubility over 0.1 mg/ml at a pH range of 4-8, preferably pH range of 5-7, such as over about 0.5 mg/ml at a pH range of 5-7, for example over about 1 mg/ml at a pH range of 5-7.

According to one embodiment, the compounds of the Invention have a limited colour, preferably they are uncoloured or pale yellow.

Preferred compounds of the present invention act primarily on src and/or lyn kinase.

According to one embodiment, the compounds of the Invention are src and/or lyn kinase inhibitors.

According to one embodiment, the compounds of the Invention bind to Src with an IC50 of less than 1 μM, advantageously less than 100 nM, even more advantageously less than 10 nM and preferably less than 1 nM.

According to one embodiment, the compounds of the Invention bind to Lyn with an IC50 of less than 1 μM, advantageously less than 100 nM, even more advantageously less than 10 nM and preferably less than 1 nM.

According to one embodiment, there are provided compositions including one or more compound of the Invention and a pharmaceutically acceptable carrier or aqueous medium.

As used herein, the term "pharmaceutically acceptable" refers to carriers that do not produce an adverse, allergic or other unwanted reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such carriers for pharmaceutical active substances is well known in the art. Examples of suitable pharmaceutical carriers are described in "Remington's Pharmaceutical Sciences" by E. W. Martin. In a preferred embodiment, the compounds of the Invention are formulated in accordance with routine procedures as a pharmaceutical composition adapted for administration to the eye. Supplementary active ingredients, such as anti-inflammatory agent, chemotherapeutic agent, anti-cancer agent, immunomodulatory agent, gene-based therapeutic vaccine, immunotherapy product, therapeutic antibody and/or protein kinase inhibitors can also be incorporated into the compositions.

According to one embodiment, the compounds of the present invention will be formulated for parenteral administration, e.g., formulated for injection via the intravenous, intramuscular, subcutaneous, or even intraperitoneal routes. The preparation of an aqueous composition that contains a compound or compounds of the Invention will be within the skill of those in the art, in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

According to another embodiment, the compounds of the present invention will be formulated for topical administration of the compounds of the Invention, especially for the treatment of ophthalmic disorders. The preparation of a composition that contains a compound or compounds of the Invention will be within the skill of those in the art, in light of the present disclosure. Typically, such compositions for topical administration can be prepared as ointment, gel or eye drops. The topical ophthalmic composition may further be an in situ gelly aqueous formulation. Such a formulation comprises a gelling agent in a concentration effective to promote gelling upon contact with the eye or with lacrimal fluid in the exterior of the eye. Suitable gelling agents include, but are not limited to, thermosetting polymers such as tetra-substituted ethylene diamine block copolymers of ethylene oxide and propylene oxide (e.g., poloxamine); polycarbophil; and polysaccharides such as gellan, carrageenan (e.g., kappa-carrageenan and iota-carrageenan), chitosan and alginate gums. The phrase "in situ gellable" as used herein embraces not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye.

According to another embodiment, the compounds of the present invention will be formulated for oral administration of the compounds of the Invention. The preparation of a composition that contains a compound or compounds of the Invention will be within the skill of those in the art, in light of the present disclosure. Typically, such compositions for oral administration can be prepared as liquid solutions or suspensions, tablets, time release capsules and other solids for oral administration.

According to another embodiment, the compounds of the present invention will be formulated for intratumoral administration of the compounds of the Invention. The preparation of a composition that contains a compound or compounds of the Invention will be within the skill of those in the art, in light of the present disclosure. Typically, such compositions for intratumoral administration can be prepared as disclosed above for the other routes of administration.

According to another embodiment, the compounds of the present invention will be combined with ophthalmologically acceptable preservatives, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. The compounds are preferably formulated as topical ophthalmic suspensions or solutions, with a pH of about 5 to 8, and more preferably from about 6.5 to about 7.5. The compounds will normally be contained in these formulations in an amount 0.001% to 5% by weight, but preferably in an amount of 0.025% to 2% by weight. Thus, for topical presentation 1 to 2 drops of these formulations would be delivered to the surface of the eye 1 to 4 times per day according to the discretion of a skilled clinician.

In another embodiment, there are provided methods of treating a disorder involving tyrosine kinase dysregulation such as disorder associated with increased vascular permeability or angiogenesis, including the administration of a therapeutically effective amount of one or more compound of the Invention to a subject in need of such treatment.

As used herein, the term "treatment" or "treating" encompasses prophylaxis and/or therapy. Accordingly the compositions and methods of the present invention are not limited to therapeutic applications and can be used in prophylaxis ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

As used herein, the terms "patient" "subject in need thereof" are meant any animal; preferably, the animal is a vertebrate; more particularly a member of the mammalian species and includes, but is not limited to, domestic animals (e.g. cows, hogs, sheep, horses, dogs, and cats), primates including humans. The terms "patient" "subject in need thereof" are in no way limited to a special disease status, it encompasses both patients who have already developed a disease of interest and patients who are not sick.

As used herein, the terms "therapeutically effective amount" are meant any amount of compound or composition that will elicit the biological response of a tissue, animal, or human, cell, organ . . . .

According to one embodiment, the said disorder involving tyrosine kinase dysregulation is a disorder associated with increased vascular permeability.

According to another embodiment, the said disorder involving tyrosine kinase dysregulation is a disorder associated with angiogenesis.

In preferred embodiment, the disorder involving tyrosine kinase dysregulation is a disorder associated with a src and/or lyn kinase dysregulation.

According to one embodiment, the said disorder involving tyrosine kinase dysregulation is selected in the group consisting of myocardial infarction, stroke, congestive heart failure, an ischemia or reperfusion injury, trauma, cancer, oedema, arthritis or other arthropathy, retinopathy or vitreoretinal disease, diabetic retinopathy, macular oedema, including diabetic macular oedema, macular degeneration, glaucoma, autoimmune disease, vascular leakage syndrome, inflammatory disease, oedema, transplant rejection, burn, or acute or adult respiratory distress syndrome (ARDS).

In another embodiment, there are provided methods of treating an ophthalmic disorder associated with increased vascular permeability, including the administration of a therapeutically effective amount of one or more compound of the Invention to a subject in need of such treatment.

In another embodiment, there are provided methods of treating a subject having or at risk of having cancer including administering to the subject a therapeutically effective amount of one or more compound of the Invention thereby treating the subject.

In another embodiment, there are provided methods of treating a subject having or at risk of having oedema and/or angiogenesis including administering to the subject a therapeutically effective amount of one or more compound of the Invention, thereby treating the subject.

In another embodiment, there are provided methods of treating a subject having or at risk of having macular degeneration including administering to the subject a therapeutically effective amount of one or more compound of the Invention, thereby treating the subject.

In another embodiment, there are provided methods of treating a subject having or at risk of having diabetic retinopathy including administering to the subject a therapeutically effective amount of one or more compound of the Invention, thereby treating the subject.

In another embodiment, there are provided methods of treating a subject having or at risk of having macular oedema, including diabetic macular oedema, including administering to the subject a therapeutically effective amount of one or more compound of the Invention, thereby treating the subject.

In another embodiment, there are provided methods of treating a subject having or at risk of having glaucoma including administering to the subject a therapeutically effective amount of one or more compound of the Invention, thereby treating the subject.

In another embodiment, there are provided methods of treating a subject having or at risk of having retinopathy including administering to the subject a therapeutically effective amount of one or more compound of the Invention, thereby treating the subject.

In another embodiment, there are provided methods of treating a subject having or at risk of having vitreoretinal disease including administering to the subject a therapeutically effective amount of one or more compound of the Invention, thereby treating the subject.

In another embodiment, there are provided methods of treating a subject having or at risk of having inflammatory disease, including administering to the subject a therapeutically effective amount of one or more compounds of the Invention, thereby treating the subject.

In yet another embodiment, there are provided methods of treating a disorder, including an ophthalmic disorder and cancer, associated with compromised vascular permeability including the administration of a therapeutically effective amount of one or more compound of the Invention in combination with an anti-inflammatory agent, chemotherapeutic agent, antitumoral agent, immunomodulatory agent, gene-based therapeutic vaccine, immunotherapy product, therapeutic antibody and/or a kinase inhibitor, to a subject in need of such treatment.

Administration of the compounds of the Invention, especially for ophthalmic applications, is preferably by topical administration. However, the invention is not limited to topical delivery in that it also includes for example intraocular and periocular injection, systemic delivery (e.g. oral or other parenteral route such as for example subcutaneous, intramuscular, intravenous administrations) or intratumoral delivery.

In yet another embodiment, there are provided methods of delivering a compound of the Invention to the back of the eye, the method including preparing a composition including a pharmaceutically effective amount of at least one compound of the Invention and delivering said composition to the eye of a subject in need of such delivery.

In yet another embodiment, there are provided methods of delivering a compound of the Invention intratumoraly, the method including preparing a composition including a pharmaceutically effective amount of at least one compound of the Invention and delivering said composition to the tumor of a subject in need of such delivery.

To prepare a composition of the Invention, and more specifically an ophthalmic composition or antitumoral composition, a therapeutically effective amount of one or more compound of the Invention is placed in a vehicle as is known in the art. For example, topical ophthalmic formulations containing steroids are disclosed in U.S. Pat. No. 5,041,434, whilst sustained release ophthalmic formulations of an ophthalmic drug and a high molecular weight polymer to form a highly viscous gel have been described in U.S. Pat. No. 4,271,143 and U.S. Pat. No. 4,407,792. Further GB 2007091 describes an ophthalmic composition in the form of a gel comprising an aqueous solution of a carboxyvinyl polymer, a water-soluble basic substance and an ophthalmic drug. Alternatively, U.S. Pat. No. 4,615,697, discloses a controlled release composition and method of use based on a bioadhesive and a treating agent, such as an anti-inflammatory agent.

The amount of the compounds of the Invention to be administered and its concentration in the compositions used in the method of the Invention depend upon the selected dissolving agent, delivery system or device, clinical condition of the patient, side effects and stability of the compound within the composition. Thus, the physician employs the appropriate preparation containing the appropriate concentration of the compounds of the Invention and selects the amount of formulation administered, depending upon clinical experience with a given patient or with similar types of patients.

In another embodiment, there are provided processes for making one or more compound of the Invention or its pharmaceutically acceptable salt, hydrate, solvate, crystal form salt and individual diastereomers thereof.

There are multiple synthetic routes for the preparation of the compounds of the invention, but all rely on chemistry known to the synthetic organic chemist. Thus, compounds represented by Formula I can be synthesized according to procedures described in the literature and are well-known to one skilled in the art. Typical literature sources are "Advanced organic chemistry", 4th Edition (Wiley), J March, "Comprehensive Organic Transformation", 2nd Edition (Wiley), R. C. Larock, "Handbook of Heterocyclic Chemistry", 2nd Edition (Pergamon), A. R. Katritzky), review articles such as found in "Synthesis", "Acc. Chem. Res.", "Chem. Rev", or primary literature sources identified by standard literature searches online or from secondary sources such as "Chemical Abstracts" or "Beilstein". Compounds of the invention can be synthesized by methods analogous to those exemplified in the Examples herein for certain representative compounds. Using the procedures described in the Examples section, and well known procedures, one skilled in the art can prepare the compounds disclosed herein.

In another embodiment, there are provided kit including packaging material and a composition contained within the packaging material, wherein the packaging material includes a label which indicates that the composition can be used for treatment of disorders associated with compromised vascular permeability and wherein the composition includes one or more compound of the Invention.

In another embodiment, there are provided kit including packaging material and a composition contained within the packaging material, wherein the packaging material includes a label which indicates that the composition can be used for treatment of disorders associated with compromised vascular permeability and selected from myocardial infarction, stroke, congestive heart failure, an ischemia or reperfusion injury, cancer, arthritis or other arthropathy, retinopathy or vitreoretinal disease, macular degeneration, autoimmune disease, vascular leakage syndrome, inflammatory disease, edema, transplant rejection, burn, or acute or adult respiratory distress syndrome (ARDS) and wherein the composition includes one or more compound of the Invention.

In one preferred embodiment, there are provided kit including packaging material and a composition contained within the packaging material, wherein the packaging material includes a label which indicates that the composition can be used for treatment of ophthalmic disorders associated with compromised vascular permeability and wherein the composition includes one or more compound of the Invention or its pharmaceutically acceptable salt, hydrate, solvate, crystal form salt and individual diastereomers thereof.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

The present invention is not to be limited in scope by the specific embodiments described herein, which are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

The following examples are given to illustrate the preparation of compounds that are the subject of this invention but should not be construed as implying any limitations to the claims. The proton magnetic resonance spectrum of each compound of the Examples was consistent with the assigned structure.

EXAMPLES

1—Synthesis of Compounds of General Formula (I)

1.1. General Method

Step A—Coupling of 6-Bromo-quinazolin-2-ylamine to 1 eq of optionally substituted B1,B2-phenyl boronic acid in a polar solvent at −100 to 300° C., most preferably 50-150° C.

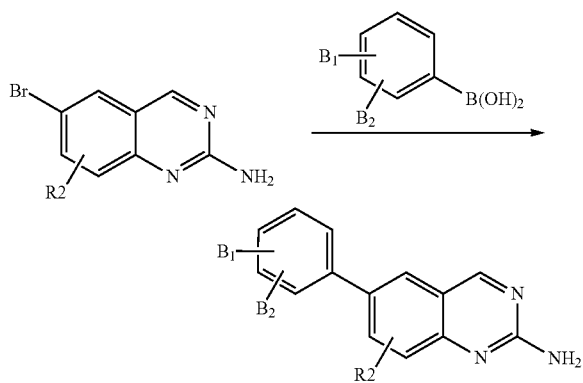

Step B—Coupling of 3 or 4-substituted bromo-phenyl to 1 eq of optionally substituted B1,B2-phenyl-quinazolin-2-ylamine in a polar solvent at −100° C. to 300° C., most preferably 50-150° C.

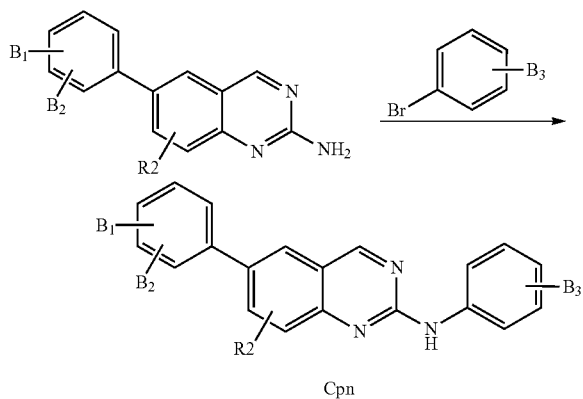

Cpn

The compounds of the formula I and also the starting materials for their preparation, are prepared by methods as described in the examples or by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the formula I. On the other hand, it is possible to carry out the reaction stepwise.

Preferably, the reaction of the compounds is carried out in the presence of a suitable solvent, which is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water. Polar solvents are in general preferred. Examples for suitable polar solvents are chlorinated hydrocarbons, alcohols, glycol ethers, nitriles, amides and sulfoxides or mixtures thereof. More preferred are amides, especially dimethylformamide (DMF).

As stated above, the reaction temperature is between about −100° C. and 300° C., depending on the reaction step and the conditions used.

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 min and 48 hrs.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

LIST OF ABBREVIATIONS AND ACRONYMS

AcOH acetic acid, anh anhydrous, atm atmosphere(s), BOC tert-butoxycarbonyl CDI 1,1'-carbonyl diimidazole, conc concentrated, d day(s), dec decomposition, DMAC N,N-dimethylacetamide, DMPU 1,3-dimethyl-3,4,5,6-tetrahydro-2(IH)-pyrimidinone, DMF N,N-dimethylformamide, DMSO dimethylsulfoxide, DPPA diphenylphosphoryl azide, EDCI 1-(3-dimethylaminopropyl)-3-ethylcarbodiimide, EtOAc ethyl acetate, EtOH ethanol (100%), Et$_2$O diethyl ether, Et$_3$N triethylannine, h hour(s), MeOH methanol, pet. ether petroleum ether (boiling range 30-60° C.), temp. temperature, THF tetrahydrofuran, TFA trifluoroAcOH, Tf trifluoromethanesulfonyl.

The compounds of general formula I of the present invention can be prepared according to the procedures of the following Steps A and B above disclosed and the examples. In all preparative methods, all starting material is known or may easily be prepared from known starting materials.

1.2. Intermediates

In all preparative methods, all starting material is known or may easily prepared from known starting materials by the following general method:

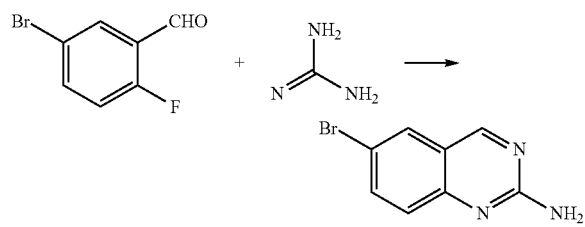

The compounds can be prepared by the general method, following procedures depicted in J. Heterocyclic Chem. 34, 385 (1997).

Synthesis of intermediate 2
6-(2-Chloro-5-methoxy-phenyl)-quinazolin-2-ylamine

To a solution of 2-chloro-5-methoxy boronic acid (14.42 g, 77.34 mmol, 1.5 eq), 6-Bromo-quinazolin-2-ylamine (11.55 g, 51.56 mmol, 1 eq) and Na2CO3 (21.86 g, 206.23 mmol, 4 eq) in a mixture of 120 ml DMF/30 ml EtOH/30 ml H2O, was added 2.311 g (5.16 mmol, 0.1 eq) of tetrakis(triphenylphosphine) palladium. The reaction was refluxed (100° C.) for 2 hours under argon. It was then cooled off to room temperature to extract the product by DCM and brine. The product is then washed with water and ether, then dried to give 9.010 g (32 mmol, 61%) of a pale yellow powder.

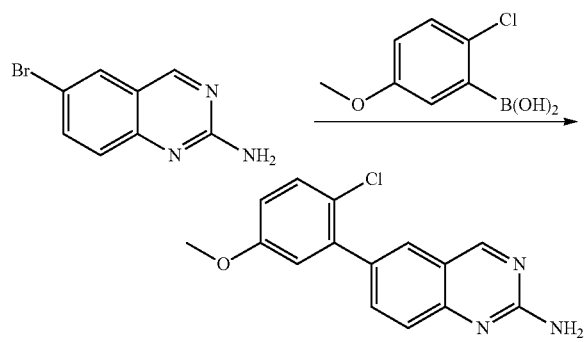

Intermediate 1
(6-(2,6-Dimethyl-phenyl)-quinazolin-2-ylamine) has been synthesized according to the method disclosed for Intermediate 2

Synthesis of Intermediate 3
3-(2-Amino-quinazolin-6-yl)-4-chloro-phenol

To a suspension of 9.010 g (31.53 mmol, 1 eq) of 6-(2-Chloro-5-methoxy-phenyl)-quinazolin-2-ylamine in 300 ml of dichloromethane cooled to 0° C. was added carefully 95 ml of a 1M solution of 1M BBr3. The solution is stirred for 16 hrs. The pH is then adjusted to pH8 by adding a saturated solution of NaHCO3. The precipitated product is filtered and washed with ether and dried to give 7.596 g (27.96 mmol, 89%) of a pale yellow powder.

| INTERMEDIATES | B1 | B2 | R2 | LC/MS |
|---|---|---|---|---|
| Intermediate 1 | 2-CH3 | 6-CH3 | H | M + 1 = 249.3 |
| intermediate 2 | 2-Cl | 5-OCH3 | H | M + 1 = 285.7 |
| Intermediate 3 | 2-Cl | 5-OH | H | M + 1 = 271.9 |
| Intermediate 4 | 2-Cl | 5-OCH3 | CH3 | M + 1 = 300.7 |
| Intermediate 5 | 2-Cl | 5-OH | CH3 | M + 1 = 286.7 |

1.3. Compounds of the Invention

Synthesis of compound of the Invention N° 6

To 52 mg (0.06 mmol, 0.03 eq) of Pd2(dba)3, 17 mg (0.03 mmol, 0.02 eq) of 5-(Di-tert-butyl-phosphanyl)-1',3',5'-triphenyl-1'H-[1,4']bipyrazolyl and 253 mg (4.52 mmol, 2.15 eq) of KOH and 3 ml tertamylacohol was added 400 µl of water and the suspension is stirred for 10 minutes. 524 mg (2.10 mmol, 1 eq) of 6-(2,6-Dimethyl-phenyl)-quinazolin-2-ylamine and 681 mg (2.52 mmol, 1.2 eq) of 1-[2-(4-Bromophenoxy)-ethyl]-pyrrolidine are then added, followed by anther 3 ml of tertamyl alcohol and 400 µl of water and the mixture is stirred at 80° C. under argon for 5 hours. The solution is evaporated and the product then purified by flash chromatography (gradient DCM/MeOH) to obtain 110 mg (0.25 mmol, 12%) of a yellow solid.

The following compounds of the Invention were made in a similar way as described above:

| Examples | Name | MS<br>NMR (200 MHz, DMSOd6) |
|---|---|---|
| compound 6 | [6-(2,6-Dimethyl-phenyl)-quinazolin-2-yl]-[4-(2-pyrrolidin-1-yl-ethoxy)-phenyl]-amine | M + 1 = 439.1<br>NMR (DMSO-d6) = 9.74 (s, 1H, NH); 9.25 (s, 1H); 7.88 (d, 2H, J = 9.06 Hz); 7.67 (m, 2H, J = 1.89 Hz, J = 8.56 Hz); 7.55 (dd, 1H, J = 1.89 Hz, J = 8.56 Hz); 7.17 (m, 3H); 6.93 (d, 2H, J = 9.06 Hz); 4.05 (t, 2H); 2.79 (t, 2H); 2.48-2.57 (m, 4H); 2.01 (s, 6H); 1.69 (m, 4H) |
| compound 7 | 4-Chloro-3-{2-[4-(2-pyrrolidin- | M + 1 = 461.1<br>(DMSO-d6) = 10.76 (s, 1H, OH); 9.96 |

-continued

| Examples | Name | MS<br>NMR (200 MHz, DMSOd6) |
|---|---|---|
| | 1-yl-ethoxy)-<br>phenylamino]-<br>quinazolin-6-yl}-<br>phenol;<br>hydrochloride | (s, 1H, NH); 9.84 (s, 1H, NH); 9.32 (s, 1H); 7.85 (m, 4H); 7.65 (d, 1H); 7.37 (d, 1H); 7.02 (d, 2H); 6.86 (m, 2H); 4.32 (t, 2H); 3.52 (t, 2H); 3.2 (m, 4H); 1.98 (m, 4H) |
| compound 8 | (R)-1-(2-{4-[6-(2,6-Dimethyl-phenyl)-quinazolin-2-ylamino]-phenoxy}-ethyl)-pyrrolidine-2-carboxylic acid | M + 1 = 483.2<br>NMR (DMSO-d6) = 10.01 (bb, 1H, CO2H); 9.83 (s, 1H, NH); 9.28 (s, 1H); 7.91 (d, 2H); 7.69 (m, 2H); 7.56 (dd, 1H); 7.18 (m, 3H); 6.98 (d, 2H); 4.48 (t, 1H); 4.32 (m, 2H); 3.22-3.84 (m, 4H); 2.50 (m, 1H); 2.01 (s, 6H); 2.16-1.81 (m, 3H) |
| compound 9 | 1-{4-[6-(2,6-Dimethyl-phenyl)-quinazolin-2-ylamino]-phenyl}-3-(2-pyrrolidin-1-yl-ethyl)-imidazolidin-2-one | M + 1 = 507.2<br>NMR (DMSO-d6) = 9.82 (s, 1H, NH); 9.27 (s, 1H); 7.93 (d, 2H); 7.70 (m, 2H); 7.54 (m, 3H); 7.18 (m, 3H); 6.98 (d, 2H); 3.79 (dd, 2H); 3.50 (m, 2H); 3.33 (t, 2H); 2.59-2.67(m, 4H); 2.01 (s, 6H); 1.71 (m, 4H) |
| compound 10 | 1-(4-{4-[6-(2,6-Dimethyl-phenyl)-quinazolin-2-ylamino]-phenyl}-piperazin-1-yl)-ethanone | M + 1 = 452.2<br>NMR (DMSO-d6) = 9.76 (s, 1H, NH); 9.24 (s, 1H); 7.85 (d, 2H); 7.66 (m, 2H); 7.53 (dd, 1H); 7.17 (m, 3H); 6.97 (d, 2H); 3.59 (m, 4H); 3.07 (m, 4H); 2.04 (s, 3H); 2.01 (s, 6H) |
| compound 11 | (4-{4-[6-(2,6-Dimethyl-phenyl)-quinazolin-2-ylamino]-phenyl}-piperazin-1-yl)-pyridin-4-yl-methanone | M + 1 = 515.2<br>NMR (DMSO-d6) = 9.72 (s, 1H, NH); 9.24 (s, 1H); 8.69 (d, 2H); 7.85 (d, 2H); 7.66 (m, 2H); 7.54 (dd, 1H); 7.44 (d, 2H); 7.17 (m, 3H); 6.97 (d, 2H); 3.79 (m, 2H); 3.42 (m, 2H); 3.19 (m, 2H); 3.08 (m, 2H); 2.01 (s, 6H) |
| compound 12 | 1-{4-[6-(2-Chloro-5-hydroxy-phenyl)-quinazolin-2-ylamino]-phenyl}-3-(2-pyrrolidin-1-yl-ethyl)-imidazolidin-2-one | M + 1 = 529.1<br>NMR 5DMSO-d6) = 9.85 (bb, 2H, NH, OH); 9.31 (s, 1H); 7.93 (m, 3H); 7.83 (dd, 1H); 7.67 (d, 1H); 7.52 (d, 2H); 7.37 (d, 1H); 6.80-8.89 (m, 2H); 3.78 (m, 2H); 3.26-3.53(m, 4H); 2.44-2.59 (m, 6H); 1.66 (m, 4H) |
| compound 13 | [(R)-1-(2-{4-[6-(2-Chloro-5-hydroxy-phenyl)-quinazolin-2-ylamino]-phenoxy}-acetyl)-pyrrolidin-3-yl]-dimethyl-ammonium; chloride | M + 1 = 518.1<br>NMR (DMSO-d6) = 11.54 (s, 1H, OH); 10.33 (s, 1H, NH); 9.42 (s, 1H); 8.01 (s, 1H); 7.89 (dd, 1H); 7.72 (m, 3H); 7.37 (d, 2H); 6.84-7.02 (m, 4H); 4.77 (s, 2H); 3.79-2.97(m, 5H); 2.76 (d, 6H); 2.24-2.38 (m, 2H) |
| compound 14 | 1-((R)-3-Dimethylamino-pyrrolidin-1-yl)-2-{4-[6-(2,6-dimethyl-phenyl)-quinazolin-2-ylamino]-phenoxy}-ethanone | M + 1 = 496.2<br>NMR (DMSO-d6) = 9.74 (s, 1H, NH); 9.26 (s, 1H); 7.86 (d, 2H); 7.66 (m, 2H); 7.55 (dd, 1H); 7.17 (m, 3H); 6.92 (dd, 2H); 4.69 (d, 2H); 3.79-2.97(m, 4H); 2.79-2.54 (m, 1H); 2.16 (d, 6H); 2.17-1.95 (m, 1H); 2.01 (s, 6H); 1.86-1.50 (m, 1H) |
| compound 15 | 1-{4-[6-(2-Chloro-5-hydroxy-phenyl)-quinazolin-2- | M + 1 = 490.1<br>NMR (DMSO-d6) = 9.87 (d, 2H, NH, OH); 9.32 (s, 1H); 7.95-7.80 (m, 4H); 7.69 (d, 1H); 7.52 (d, 2H); 7.37 (d, 1H); 6.84 (m, 2H); 3.81(t, 2H); 3.49 (m, 4H); 3.34 (m, 5H) |

-continued

| Examples | Name | MS NMR (200 MHz, DMSOd6) |
|---|---|---|
| | ylamino]-phenyl}-3-(2-methoxy-ethyl)-imidazolidin-2-one | |
| compound 16 | 3-{2-[4-(2-Azepan-1-yl-ethoxy)-phenylamino]-quinazolin-6-yl}-4-chloro-phenol | M + 1 = 489.1<br>NMR (DMSO-d6) = 9.89 (bb, 1H, OH); 9.78 (s, 1H, NH); 9.30 (s, 1H); 7.84 (m, 4H); 7.64 (d, 1H); 7.37 (d, 1H); 6.87 (m, 4H); 4.01 (t, 2H); 2.83 (t, 2H); 2.68 (m, 4H); 1.54 (m, 8H) |
| compound 17 | [6-(2,6-Dimethyl-phenyl)-quinazolin-2-yl]-(4-piperazin-1-yl-phenyl)-amine | M + 1 = 410.1<br>NMR (DMSO-d6) = 9.72 (s, 1H, NH); 9.25 (s, 1H); 7.86 (d, 2H); 7.66 (m, 2H); 7.57 (dd, 1H); 7.17 (m, 3H); 6.99 (d, 2H); 3.20 (m, 8H); 2.01 (s, 6H) |
| Compound 18 | 1-(2-{4-[6-(2-Chloro-5-hydroxy-phenyl)-8-methyl-quinazolin-2-ylamino]-phenoxy}-ethyl)-pyrrolidinium; chloride | NMR (DMSO-d6) = 10.88 (bb, 1H, OH); 10.0(s, 1H, NH); 9.31 (s, 1H); 7.99 (d, 2H); 7.75 (d, 2H); 7.36 (d, 1H); 7.04 (d, 2H); 6.81-6.88 (m, 2H); 4.35 (t, 2H); 3.55 (m, 4H); 3.11 (m, 2H); 2.63 (s, 3H); 1.97 (m, 4H) |
| compound 19 | 4-Chloro-3-[2-(3-hydroxymethyl-phenylamino)-8-methyl-quinazolin-6-yl]-phenol | M + 1 = 392.0<br>NMR (DMSO-d6) = 9.87 (bb, 2H); 9.22 (s, 1H); 8.07 (s, 1H); 7.79 (d, 1H); 7.66 (d, 2H); 7.25 (m, 2H); 6.80 (m, 3H); 5.08 (bb, 1H); 4.43 (s, 2H); 2.57 (s, 3H) |

2—Solubility Analysis of Compounds of the Invention

Solubility of Compounds was determined in aqueous medium using the following procedure.

Two mg of Compound was added to 200 µl buffer (acetic acid/KOH) solution at pH 5. Solution was then stirred for 24 h at room temperature and then centrifuged 10 min at 16,000 rpm. Corresponding supernatants were analyzed by HPLC and UV detection. Calculation of a given Compound concentration was performed by reporting area under the experimental slope onto a calibration slope obtained separately using DMSO-solubilised Compound at different concentrations.

The tested compounds are:

The reference compound in the followings is as disclosed in WO2005096784 (compound CL)

TABLE 1

| Compound n° | Solubility (pH 5) in % | Solubility (pH 5) in mg/ml | Colour |
|---|---|---|---|
| Reference Base form | <0.001 | <0.01 | Bright red |
| Reference Chlorhydrate | 0.075 | 0.75 | Bright red |
| 6 Chlorhydrate | 0.09 | 0.9 | Pale yellow |
| 7 Chlorhydrate | 0.19 | 1.9 | Pale yellow |
| 7 base form | 0.03 | 0.34 | Yellow |
| 8 Chlorhydrate | 1 | 10 | Pale yellow |
| 8 base form | 0.04 | 0.4 | Orange |
| 9 Chlorhydrate | 0.35 | 3.5 | Pale yellow |
| 12 Chlorhydrate | 0.45 | 4.5 | Pale yellow |
| 13 base form | 0.03 | 0.29 | Pale green |
| 14 base form | 0.01 | 0.14 | Pale yellow |
| 16 base form | 0.05 | 0.5 | Pale yellow |
| 17 base form | 0.63 | 6.3 | brown |
| 18 Chlorhydrate | 0.67 | 6.7 | Pale yellow |

3—Measurement of Inhibition Constants of the Compounds of the Invention

The screening and profiling experiments described here were performed using Caliper Life Sciences' proprietary LabChip™ technology. Caliper LC3000 and EZ Reader II instruments are widely used throughout the drug discovery process for assay development, primary screening, selectivity screening, generation of Structure-Activity Relationships (SARs) and Mechanism of Action (MOA) studies. The Lab-Chip™ technology is particularly well suited for enzymatic 'targets' such as kinases, proteases, phosphatases, histone deacetylases (HDAC), phosphodiesterases (PDE), and acyl-transferases. The key benefit of the technology is the separation and direct measurement of substrates and products, which allows for higher signal-to-noise ratios and fewer false positive/negative results. This direct measurement also allows for the identification and elimination of enzymatic activities that are not associated with the kinase reaction of interest.

General:

The off-chip incubation mobility-shift kinase assay uses a microfluidic chip to measure the conversion of a fluorescent peptide substrate to a phosphorylated product. The reaction mixture, from a microtiter plate well, is introduced through a capillary sipper onto the chip, where the nonphosphorylated substrate and phosphorylated product are separated by electrophoresis and detected via laser-induced fluorescence. The signature of the fluorescence signal over time reveals the extent of the reaction. The phosphorylated product migrates through the chip faster than the non-phosphorylated substrate, and signals from the two forms of the peptide appear as distinct peaks. Caliper's data analysis software (HTSWA) determines peak heights, from which the ratio of product to the peak sum P/(P+S) and percent (%) conversion is calculated. This value is used to compare compound wells to control wells present on the plate, and thereby determine the % inhibition values for the compound. The formula used to calculate % inhibition is as follows, where $C_{100\%}$ is the average % conversion of the 100% activity wells and $C_{0\%}$ is the average % conversion of the 0% activity wells:

$$(1-(\% \text{ conversionofsample}-C_{0\%})/(C_{200}\%-C_0\%))*100$$

Specific:

LC3000 Src and Lyn Assays

Compounds were dissolved in 100% DMSO and diluted to 25× the final desired screening concentration. Serial dilutions were performed to obtain the concentrations specified for particular studies. One μL of each concentration was transferred, in duplicate, to a 384-well Greiner microtiter plate. Generally, 12 μL of enzyme buffer containing purified kinase (various suppliers), 100 mM HEPES, pH 7.5, 1 mM DTT (Calbiochem, 2333153), 10 mM $MgCl_2$ (Sigma, M-1028) or 10 mM $MnCl_2$ (Sigma, M-1787) (assay specific), and 0.002% Brij-35 (Sigma, B4184) was added to each well. Compound and enzyme were allowed to pre-incubate for 15 minutes. 12 μL of peptide/ATP buffer containing 100 mM HEPES, pH 7.5, 1.5 μM fluorescein-labeled peptide (specific to kinase of interest), ATP (at $K_M$ apparent, Sigma, A9187), and 0.002% Brij-35 was then added to each well to initiate the reaction. Generally, reactions were incubated for 1-1.5 hours at room temperature to obtain adequate (15-40%) conversion of peptide to phosphorylated product in the linear range of the reaction. Reactions were terminated with the addition of 45 μL of Stop Buffer (containing 20 mM EDTA). Plates were then read on the LabChip 3000 using a 12-sipper LabChip. % conversion values and % inhibition values were obtained as described and $IC_{50}$ curves of compounds were generated using Graphpad Prism Version 4 or 5.01. A nonlinear curve fit using the sigmoidal dose response—variable slope fit was used to graph $IC_{50}$ curves and determine $IC_{50}$ values and hillslopes.

It has been shown that the compounds of the Invention have 1050 against Src and Lyn kinases of <10 nM.

4—Cell-Based Assays of Compounds of the Invention 4.1—CellTiter-Glo (ATP) Viability/Proliferation Assay MDA-MB-231 is a human breast cancer cell line which is highly dependent on Src kinase pathway for viability and proliferation. Thus, Compounds of the present invention were evaluated for their capacity to reduce viability/proliferation of MDA-MB-231 cells, using two different methods that both address cell metabolic activity. In addition, some Compounds of the present invention were tested for their inhibitory against VEGF-induced proliferation of human vascular endothelial cells (HUVECs).

Assay Characteristics:

MDA-MB-231 cells are maintained as adherent cultures of no greater than 80% confluent in 185 $cm^2$ vented culture flask in the medium specified for the cell line supplemented with 10% fetal bovine serum (FBS) at 37° C. in 5% $CO_2$. For proliferation assays the adherent cells are collected from culture flask with typsin-EDTA and resuspended in respective medium containing 0.1%-5% FBS for assay.

The cellular content of ATP (CellTiter-Glo reagent from Promega) is measured by luminescent emission based on the following principle:

In the presence of ATP (provided by the cell) luciferin is converted to oxyluciferin and light is emitted. The ATP content within the cell is proportional to the amount of oxyluciferin and luminescence produced.

Incubation Conditions:

0.1 ml of cells in suspension at 1,000 cells per 0.1 ml is plated on white flat bottom 96 well plates. Cells are allowed to adhere to plates for 2-4 hours before the addition of test compounds.

0.05 ml of test compounds suspended in medium are added to wells to give final volumes of 0.15 ml. Cultures are incubated with the test compounds for 3-4 days before the cultures are assayed for cell viability. If incubation periods are longer than 4 days the final culture volume should be increased to 0.2 ml.

At the termination of treatments 0.05 ml of the culture medium are removed from each well with a multichannel pipetter, pipetting from the surface of the well.

In low light 0.1 ml of the CellTiter-Glo reagent is added to each well and the contents of each well are gently mixed by pipetting up and down. (Cover plates with foil until each plate is read on the Envision plate reader.)

Reading:

The luminescence is read on an Envision 2103 Multi-label Reader (PerkinElmer)

Calculation of Data:

Cell proliferation is expressed as percent of control wells (untreated).

It has been shown that the compounds of the Invention inhibit cell proliferation with an IC50<500 nM.

4.2—WST-1 (Mitochondrial Metabolism) Viability/Proliferation Assay

Assay Characteristics:

The assay measures mitochondrial metabolic activity of cultured cells is based on the rate of conversion of WST-1 substrate to a product with an optical density measured at 440 nm.

MDA-MB-231 are maintained as adherent cultures of no greater than 80% confluent in 185 $cm^2$ vented culture flask in the medium specified for the cell line supplemented with 10% fetal bovine serum (FBS) at 37° C. in 5% $CO_2$. For proliferation assays the adherent cells are collected from culture flask with typsin-EDTA and resuspended in respective medium containing 0.1%-5% FBS for assay.

WST-1 assay (WST-1 reagent from Roche) is based on the mitochondrial metabolism of the substrate (4-[3-(4-Iodophenyl)-2-(4-nitrophenyl)-2H-5-tetrazolio]-1,3-benzene disulfonate) to formazan and measurement of its absorbance at 440 nm.

Incubation Conditions:

Aliquots of 0.1 ml of cells are plated into wells. Cells are plated at a density of 500-1,000 cells per 0.1 ml on clear flat bottom 96-well plates. Cells are allowed to adhere to plates for 2-4 hours before the addition of test compounds.

0.05 ml of test compounds suspended in medium are added to wells to give final volumes of 0.15 ml. Cultures are incubated with the test compounds for 3-4 days before the cultures are assayed for cell viability. If incubation periods are longer than 4 days the final culture volume showed be increased to 0.2 ml.

At the termination of treatments 0.015 ml of the WST-1 solution is added to each well. Plates are returned to the $CO_2$ incubator and incubated at 37° C. for 1-3 hours. After incubation, the plates are removed from the incubator and placed on a micro-titer plate shaker and gently shaken for 2 minutes.

Readings:

The optical density at 440 nm of each well is determined using a Spectra-max plus 384 plate reader.

Calculation of Data:

Cell proliferation is expressed as percent of control wells (untreated).

It has been shown that the compounds of the Invention inhibit proliferation with an IC50<500 nM.

5. In Vivo Data

Inhibition of Vascular Leakage in a Rabbit Model of Blood-Retinal Barrier Breakdown Intravitreal injection of VEGF in the rabbit eye produces massive retinal vascular leakage (Edelman and Lutz, 2003, Invest. Ophthalmol. Vis. Sci. 2003; 44:ARVO e-abstract No. 328). Based on said animal model, we investigated the efficacy of topical administration of compound 7 of the invention in reducing the retinal leakage in a VEGF-induced blood retinal barrier breakdown in the rabbit.

During four days, 3% test compound 7 (30 mg/ml, 10% PEG 400, 87% labrafil) or control items without compound of the Invention were administered 4 times daily by topical administration (50 µl) in the right eye of five rabbits.

On day two, animals received a single intravitreal injection of 50 µl (500 ng) recombinant human VEGF 165 (RD systems) into right eye.

Forty-seven hours after the VEGF challenge (day four), fluorescein was injected via the marginal ear vein and circulate during one hour.

Breakdown of the blood-retinal barrier was evaluated 48 h after VEGF challenge by measuring fluorescein contents into the vitreoretinal compartment using non-invasive scanning ocular fluorophotometry.

Results

We found that the compound of the Invention reduced vascular leakage by 41% compared to control providing evidence that the compounds according to the Invention are useful to reduce vascular permeability, and more particularly vascular permeability associated with vitreo/retinal diseases such as diabetic retinopathy, retinal vein occlusion or wet age-related macular degeneration.

Inhibition of Vascular Leakage in a Rat Model of Blood-Retinal Barrier Breakdown We investigated the efficacy of topical administration of compound II of the invention in reducing the retinal leakage in a VEGF-induced blood retinal barrier breakdown in the rat.

Rats were treated by a single intravitreal injection of 5 µl (100 ng) recombinant human VEGF164 (RD Systems) into each eye.

During twenty-seven hours following VEGF injection, 0.51% test compound II of the Invention (5.1 mg/ml buffer pH 5 with 30% cyclodextrin) and control without compound of the Invention were administered six times by topical administration (10 µl) in eyes of sixteen rats.

Twenty-seven hours later after the VEGF challenge, Evans blue dye (45 mg/kg) was injected intravenously and the dye was allowed to circulate during two hours.

Then, each rat was infused with 0.05M citrate buffer pH 3.5 (37° C.) for 2 minutes to allow clearance of the dye. Immediately after said perfusion, both eyes were enucleated and Evans blue dye was extracted by incubating each retina in formamide (Qaum et al Invest. Ophthalmol. Vis. Sci. 2001, Vol 42, No 10). Afterward, the absorbance was measured with a spectrophotometer at 620 nm.

Breakdown of blood-retinal barrier was proportional to the concentration of Evans blue in the retina normalized by Evans blue concentrations in the plasma.

Results

We found that the compound of Invention reduced vascular leakage by 56% compared to control providing evidence that the compounds of the Invention are useful to reduce vascular permeability, and more particularly vascular permeability associated with vitreo/retinal diseases such as diabetic retinopathy.

The invention claimed is:

1. A compound having the structure (I) as well as pharmaceutically acceptable salt thereof:

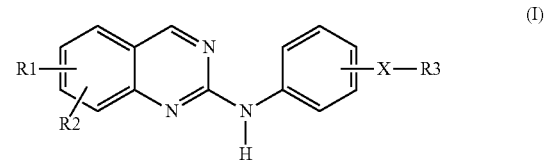

wherein:

R1 is phenyl and R2 is hydrogen or methyl,

R3 is hydrogen, C1-C4 alkyl, cycloalkyl, heterocycloalkyl, aryl, heteroaryl, —CN, —CF$_3$, —OR4, —OCOR4-COR4, —NR4R5, —NR4COR5, —NR4COOR5, —(C1-C4 alkyl)OR4, —(C1-C4 alkyl)COR4, —(C1-C4 alkyl)NR4R5, —(C1-C4 alkyl)NR4COR5, —(C1-C4 alkyl)NR4COOR5, X is a bond, or (CH$_2$)aW(CH$_2$)b, (CH$_2$)aW(CH$_2$)bY(CH$_2$)c or —[(CH$_2$)aW(CH$_2$)b]m-(Z)e-[(CH$_2$)cY(CH$_2$)d]n wherein:

a, b, c and d are independently 0, 1, 2 or 3, e is 0, 1 or 2, and n and m are independently 0 or 1, and W is —CO—, —O—, —SO$_2$—, —CH$_2$—, —CHOH—, —NR6-, NR7CONR8 or NR7SO$_2$NR8, and Y is —CO—, —O—, —SO$_2$—, —CH$_2$—, —CHOH— or —NR6-, NR7CONR8 or NR7SO$_2$NR8 and Z is selected from the group consisting of cycloalkyl, heterocycloalkyl, aryl and heteroaryl, and when e is 2, then each Z moiety is selected independently from one another, R4, R5 and R6 are independently hydrogen, C1-C4 alkyl and where R4 and R5 together can form a 5-7 membered ring, R7 and R8 are independently hydrogen, C1-C4 alkyl and where R7 and R8 together can form a 5-7 membered ring, wherein
cycloalkyl is a saturated monocyclic carbocycle containing from 3 to 7 carbon atoms;
heterocycloalkyl is a saturated mono- or bicyclic heterocycle having from 3 to 14 ring members, which contains one or more heteroatom ring members selected from nitrogen, oxygen and sulphur and which is optionally substituted with R9 and/or R10 moities;
aryl is a mono- or bicyclic aromatic carbocycles, optionally substituted with R9 and/or R10 moities;
heteroaryl is an aromatic mono- or bicyclic heterocycle having from 5 to 10 ring members, which contains one or more heteroatom ring members selected from nitrogen, oxygen and sulphur and which is optionally substituted with R9 and/or R10 moities;
and R9/R10 are independently selected from hydrogen, cycloalkyl, heterocycloalkyl, aryl, heteroaryl, —CN, -halogen, —CF3, =O, —OR4, —NR4COR5, —NR4COOR5, —(C1-C4 alkyl)OR4, —(C1-C4 alkyl)NR4R5, —(C1-C4 alkyl)NR4COR5, —(C1-C4 alkyl)NR4COOR5, —COOH, COOR4 with R4 and R5 as defined above.

2. The compound of claim 1, wherein the cycloalkyl is selected from cyclopropyl, cyclobutyl, and cyclopentyl.

3. The compound of claim 1, wherein the heterocycloalkyl has 5 to 10 ring members.

4. The compound of claim 3, wherein the heterocycle has 5 to 6 ring members.

5. The compound of claim 3, wherein the heterocycloalkyl is selected from pyrrolidine, piperidine, piperazine and morpholine, each of which is optionally substituted with R9 and/or R10 moities.

6. The compound of claim 1, wherein the aryl is selected from phenyl, 1-naphthyl, and 2-naphthyl.

7. The compound of claim 1, wherein the heteroaryl has 5 to 6 ring members.

8. The compound of claim 1, wherein the heteroaryl is selected from pyridine, indole, benzofuran, oxazole, triazole, and pyrimidine, each of which is optionally substituted with R9 and/or R10 moities.

9. The compound claim 1 wherein R1 is substituted with R9 and R10 and wherein R9/R10 is C1-C4 alkyl, halogen or —OH.

10. The compound of claim 1 wherein R1 is a phenyl and is substituted with R9 and R10 in positions 2, 5 or 6.

11. The compound of claim 1, wherein X is a bond.

12. The compound of claim 1, wherein X is (CH$_2$)aW(CH$_2$)b where a is 0, b is 2, W is —O—.

13. The compound of claim 1, wherein X is (CH$_2$)aW(CH$_2$)bY(CH$_2$)c where a is 0, b is 1 and c is 0, W is —O— and Y is —CO—.

14. The compound of claim 1, wherein X is —[(CH$_2$)aW(CH$_2$)b]m-Z-[(CH$_2$)cY(CH$_2$)d]n where m is 0, n is 1, c is 0, d is 0 or 2, Y is —CO— or is absent and Z is imidazoline-2-one or a piperazine.

15. The compound of claim 1, wherein R3 is C1-C4 alkyl.

16. The compound of claim 15, wherein R3 is —CH$_3$.

17. The compound of claim 1, wherein R3 is a C1-C4 alkyl group.

18. The compound of claim 17, wherein R3 is —CH$_3$.

19. The compound of claim 17, wherein R3 is substituted with R9.

20. The compound of claim 19, wherein where R9 is —OH.

21. The compound of claim 1, wherein R3 is a heteroaryl group.

22. The compound of claim 21, wherein R3 is pyridine.

23. The compound of claim 1, wherein R3 is a heterocycloalkyl.

24. The compound of claim 23, wherein R3 is pyrrolidine, piperidine, azepine, piperazine or morpholine.

25. The compound of claim 24, wherein R3 is pyrrolidine.

26. The compound of claim 1, wherein R3 is a heterocycloalkyl substituted with R9.

27. The compound of claim 26, wherein R9 is —COOH, COOR4, or —N[CH$_3$]$_2$.

28. The compound of claim 1, selected in the group consisting of:
- [6-(2,6-Dimethyl-phenyl)-quinazolin-2-yl]-[4-(2-pyrrolidin-1-yl-ethoxy)-phenyl]-amine;
- 4-Chloro-3-{2-[4-(2-pyrrolidin-1-yl-ethoxy)-phenylamino]-quinazolin-6-yl}-phenol;
- (R)-1-(2-{4-[6-(2,6-Dimethyl-phenyl)-quinazolin-2-ylamino]-phenoxy}-ethyl)-pyrrolidine-2-carboxylic acid;
- 1-{4-[6-(2,6-Dimethyl-phenyl)-quinazolin-2-ylamino]-phenyl}-3-(2-pyrrolidin-1-yl-ethyl)-imidazolidin-2-one;
- 1-(4-{4-[6-(2,6-Dimethyl-phenyl)-quinazolin-2-ylamino]-phenyl}-piperazin-1-yl)-ethanone;
- (4-{4-[6-(2,6-Dimethyl-phenyl)-quinazolin-2-ylamino]-phenyl}-piperazin-1-yl)-pyridin-4-yl-methanone;
- 1-{4-[6-(2-Chloro-5-hydroxy-phenyl)-quinazolin-2-ylamino]-phenyl}-3-(2-pyrrolidin-1-yl-ethyl)-imidazolidin-2-one;
- 2-{4-[6-(2-Chloro-5-hydroxy-phenyl)-quinazolin-2-ylamino]-phenoxy}-1-((R)-3-dimethylamino-pyrrolidin-1-yl)-ethanone;
- 1-((R)-3-Dimethylamino-pyrrolidin-1-yl)-2-{4-[6-(2,6-dimethyl-phenyl)-quinazolin-2-ylamino]-phenoxy}-ethanone;
- 1-{4-[6-(2-Chloro-5-hydroxy-phenyl)-quinazolin-2-ylamino]-phenyl}-3-(2-methoxy-ethyl)-imidazolidin-2-one;
- 3-{2-[4-(2-Azepan-1-yl-ethoxy)-phenylamino]-quinazolin-6-yl}-4-chloro-phenol;
- [6-(2,6-Dimethyl-phenyl)-quinazolin-2-yl]-(4-piperazin-1-yl-phenyl)-amine;
- 4-Chloro-3-{8-methyl-2-[4-(2-pyrrolidin-1-yl-ethoxy)-phenylamino]-quinazolin-6-yl}-phenol;
- [(R)-1-(2-{4-[6-(2-Chloro-5-hydroxy-phenyl)-quinazolin-2-ylamino]-phenoxy}-acetyl)-pyrrolidin-3-yl]-dimethyl-ammonium;
- [(R)-1-(2-{4-[6-(2-Chloro-5-hydroxy-phenyl)-quinazolin-2-ylamino]-phenoxy}-acetyl)-pyrrolidin-3-yl]-dimethyl-ammonium;
- 4-Chloro-3-[2-(3-hydroxymethyl-phenylamino)-8-methyl-quinazolin-6-yl]-phenol;
- (R)-1-(2-{4-[6-(2-Chloro-5-hydroxy-phenyl)-8-methyl-quinazolin-2-ylamino]-phenoxy}-ethyl)-pyrrolidine-2-carboxylic acid;
- 1-{4-[6-(2-Chloro-5-hydroxy-phenyl)-8-methyl-quinazolin-2-ylamino]-phenyl}-3-(2-pyrrolidin-1-yl-ethyl)-imidazolidin-2-one;
- (R)-1-[2-(3-{4-[6-(2-Chloro-5-hydroxy-phenyl)-8-methyl-quinazolin-2-ylamino]-phenyl}-2-oxo-imidazolidin-1-yl)-ethyl]-pyrrolidine-2-carboxylic acid;
- 1-{4-[6-(2-Chloro-5-hydroxy-phenyl)-8-methyl-quinazolin-2-ylamino]-phenyl}-3-[2-((R)-3-dimethylamino-pyrrolidin-1-yl)-ethyl]-imidazolidin-2-one;
- 1-(4-{4-[6-(2-Chloro-5-hydroxy-phenyl)-8-methyl-quinazolin-2-ylamino]-phenyl}-piperazin-1-yl)-ethanone;

(4-{4-[6-(2-Chloro-5-hydroxy-phenyl)-8-methyl-quinazolin-2-ylamino]-phenyl}-piperazin-1-yl)-pyridin-4-yl-methanone;

(4-{4-[6-(2-Chloro-5-hydroxy-phenyl)-8-methyl-quinazolin-2-ylamino]-phenyl}-piperazin-1-yl)-pyridin-3-yl-methanone;

(4-{4-[6-(2-Chloro-5-hydroxy-phenyl)-8-methyl-quinazolin-2-ylamino]-phenyl}-piperazin-1-yl)-pyridin-2-yl-methanone;

2-{4-[6-(2-Chloro-5-hydroxy-phenyl)-8-methyl-quinazolin-2-ylamino]-phenoxy}-1-((R)-3-dimethylamino-pyrrolidin-1-yl)-ethanone; and and a salt of any thereof.

* * * * *